United States Patent
He et al.

(10) Patent No.: US 12,385,090 B2
(45) Date of Patent: Aug. 12, 2025

(54) METHOD FOR SEQUENCING LONG-FRAGMENT NUCLEIC ACID

(71) Applicant: BGI SHENZHEN, Guangdong (CN)

(72) Inventors: Lin He, Guangdong (CN); Sha Liao, Guangdong (CN); Chongjun Xu, Guangdong (CN); Wenwei Zhang, Guangdong (CN); Ao Chen, Guangdong (CN)

(73) Assignee: BGI SHENZHEN (CN)

( * ) Notice: Subject to any disclaimer, the term of this patent is extended or adjusted under 35 U.S.C. 154(b) by 1105 days.

(21) Appl. No.: 17/338,708

(22) Filed: Jun. 4, 2021

(65) Prior Publication Data

US 2021/0324466 A1 Oct. 21, 2021

Related U.S. Application Data

(63) Continuation of application No. PCT/CN2018/119857, filed on Dec. 7, 2018.

(51) Int. Cl.
*C12Q 1/6874* (2018.01)

(52) U.S. Cl.
CPC .................. *C12Q 1/6874* (2013.01)

(58) Field of Classification Search
None
See application file for complete search history.

(56) References Cited

U.S. PATENT DOCUMENTS

| | | | |
|---|---|---|---|
| 9,689,032 B2 | 6/2017 | Zhou et al. | |
| 10,036,013 B2 | 7/2018 | Kim | |
| 10,221,436 B2 | 3/2019 | Hardenbol et al. | |
| 10,443,087 B2 | 10/2019 | Rigatti et al. | |
| 10,557,158 B2 | 2/2020 | Hardenbol et al. | |
| 10,801,062 B2 | 10/2020 | Zhou et al. | |
| 10,865,410 B2 | 12/2020 | Kim | |
| 11,299,765 B2 | 4/2022 | Rigatti et al. | |
| 11,414,688 B2 | 8/2022 | Hardenbol et al. | |
| 2009/0062129 A1 | 3/2009 | McKernan et al. | |
| 2012/0165205 A1 | 6/2012 | West | |
| 2012/0252682 A1 | 10/2012 | Zhou et al. | |
| 2013/0165328 A1 | 6/2013 | Previte et al. | |
| 2014/0065604 A1 | 3/2014 | Zhou et al. | |
| 2014/0315724 A1* | 10/2014 | Zhou | C12Q 1/6869 435/6.1 |
| 2015/0051088 A1 | 2/2015 | Kim | |
| 2015/0051116 A1 | 2/2015 | Kim | |
| 2016/0257984 A1 | 9/2016 | Hardenbol et al. | |
| 2017/0130260 A1 | 5/2017 | Rigatti et al. | |
| 2017/0204457 A1 | 7/2017 | Crawford et al. | |
| 2018/0334671 A1 | 11/2018 | Kim | |
| 2019/0169666 A1 | 6/2019 | Hardenbol et al. | |
| 2020/0002747 A1 | 1/2020 | Rigatti et al. | |
| 2020/0190551 A1 | 6/2020 | Hardenbol et al. | |
| 2021/0062186 A1 | 3/2021 | Kim | |
| 2021/0180123 A1 | 6/2021 | Zhou et al. | |
| 2022/0195495 A1 | 6/2022 | Rigatti et al. | |

FOREIGN PATENT DOCUMENTS

| | | |
|---|---|---|
| CN | 101495654 A | 7/2009 |
| CN | 102534040 A | 7/2012 |
| CN | 102766689 A | 11/2012 |
| CN | 103917654 A | 7/2014 |
| CN | 104404160 A | 3/2015 |
| CN | 104711250 A | 6/2015 |
| CN | 105506063 A | 4/2016 |
| CN | 105525357 A | 4/2016 |
| CN | 105624272 A | 6/2016 |
| CN | 105917036 A | 8/2016 |
| CN | 106715693 A | 5/2017 |
| CN | 107427808 A | 12/2017 |
| CN | 108239669 A | 7/2018 |
| CN | 108330186 A | 7/2018 |
| WO | 0166802 A1 | 9/2001 |

OTHER PUBLICATIONS

Chen et al, The History and Advances of Reversible Terminators Used in New Generations of Sequencing Technology, Genomics Proteomics & Bioinformatics, 11(1), 34-40 (Year: 2013).*
Chinese Patent Office, Office Action dated Jun. 6, 2023, for corresponding Chinese Patent Application No. 201880098533.4 (English translation provided).

* cited by examiner

*Primary Examiner* — Juliet C Switzer
*Assistant Examiner* — Brian Ellis Young
(74) *Attorney, Agent, or Firm* — Duane Morris LLP

(57) ABSTRACT

Provided is a method for sequencing a long-fragment nucleic acid. The nucleic acid molecules each containing a long insert, a first sequencing adapter, and a second sequencing adapter, is used to construct a sequencing library, and the sequencing is performed in segments to sequence the nucleic acids having the long inserts.

12 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: repressor primer

<400> SEQUENCE: 1
gcgtagcgcg gaaccatggt tccgcgctac ggctcacaga acgacatggc tacgatccga      60
ctt                                                                    63
```

METHOD FOR SEQUENCING LONG-FRAGMENT NUCLEIC ACID

CROSS-REFERENCE TO RELATED APPLICATIONS

This application is a continuation of International Application No. PCT/CN2018/119857, filed on Dec. 7, 2018, the disclosure of which is hereby incorporated by reference in its entirety.

TECHNICAL FIELD

The present disclosure relates to the field of gene sequencing, in particular to a method for sequencing long-fragment nucleic acids.

BACKGROUND

In 1977, Sanger invented the dideoxy terminal termination sequencing method, which became the representative of the first-generation sequencing technology. In 2001, relying on the first-generation sequencing technology, the human genome draft was completed. The Sanger sequencing method has the characteristics of simple experimental operation, intuitive and accurate results and short experimental period, and thus it has a wide range of applications in clinical gene mutation detection and genotyping that require high timeliness of detection results. However, the Sanger sequencing has low throughput and high cost, which limits its application in large-scale gene sequencing.

The second-generation sequencing technology emerged, in order to overcome the shortcomings of the Sanger sequencing method. Compared with the first-generation sequencing technology, the second-generation sequencing technology has the advantages of high throughput, low cost and high degree of automation, and thus it is suitable for large-scale sequencing. At present, the developed second-generation sequencing technology mainly involves technologies of sequencing by ligation (SBL) and sequencing by synthesis (SBS). Typical examples of these sequencing technologies include the Roche 454 sequencing method, the SOLID sequencing method developed by Applied Biosystems, the combinatorial probe-anchor ligation (cPAL) method independently developed by Complete Genomics, the combinatorial probe-anchor synthesis (cPAS) method developed by BGI®, the ILLUMINA® sequencing method jointly developed by ILLUMINA® and SOLEXA® technology, and the like. The sequencing detection methods mainly include the electrochemical method, the optical signal detection method, etc., among which the mainstream detection method is the optical signal detection. Due to the hardware requirements of the second-generation sequencing technology, the instruments are relatively large, which is not conducive to carrying and handling. Although the third-generation sequencing technology can overcome the disadvantages in terms of huge size of the second-generation sequencing technology, the sequencing error rate thereof is relatively high, which limits its promotion.

Therefore, the method for gene sequencing, especially the determination of long-fragment nucleic acids, is still required to be further improved.

SUMMARY

The present disclosure provides a method, which has low cost and can realize sequencing of long-fragment nucleic acids, in order to solve one of the technical problems in related technologies at least to a certain extent.

In the research, the inventors of the present disclosure found that, in the field of gene sequencing, long sequence reading has many advantages, for example, it is beneficial to the study of transcriptome, and a full-length transcriptome can be directly obtained. However, the read length has always been the weakness of the second-generation sequencing, and thus the second-generation sequencing can hardly solve the problems such as highly heterozygous genome, highly repetitive sequence, high GC region, copy number variation, and large structural variation. The second-generation sequencing, ILLUMINA® HISEQ® 2500 sequencing platform, is based the SBS of DNA single molecule clusters and its proprietary reversible termination chemical reaction technology. The sequencing based on this platform requires to build a library by adding universal adapters (P7 and P5 adapters) with known sequences on both ends of DNA fragments, and then load the library on the sequencing chip Flowcell, which is a glass plate with multiple lanes. Each lane can test one sample or a mixture of multiple samples, and it is randomly filled with oligonucleotides which can be complementary paired with or matched the adapters on both ends of the library. During sequencing, the prepared random fragments of genomic DNA are attached to an optically transparent glass surface (i.e., the Flowcell). After these DNA fragments are elongated and bridge-amplified, hundreds of millions of clusters are formed on the Flowcell, and each cluster is a single molecular cluster with thousands of identical template DNAs. Then, the template DNAs to be detected can be sequenced with the reversible termination SBS (sequencing by synthesis) technology using four special deoxynucleotides with fluorescent groups. That is, during the base elongation, only one correct complementary base can be paired in each cycle reaction, and the type of base is confirmed based on the four different fluorescent signals, thereby guaranteeing the final nucleic acid sequencing quality. After multiple cycles, the complete nucleic acid sequence can be read. This new method ensures the highly accurate and real sequencing of one base after another, and thus provides a good solution for the sequencing of homopolymers and repetitive sequences.

On basis of the above, the inventors creatively determined the nucleic acid sequence containing a long insert by segmental sequencing. For example, a base sequence of about 300 bp is sequenced as one fragment, and then the long fragment can be sequenced by sequence splicing.

To achieve the above purpose, the technical solution of the present disclosure is realized by the following steps.

According to a first aspect of the present disclosure, the present disclosure provides a method for determining a nucleic acid sequence of a predetermined region of a nucleic acid molecule to be detected. The nucleic acid molecule to be detected includes an insert, and a length of the insert is greater than a read length of a sequencer. The method includes: providing two ends of the insert with a first sequencing adapter and a second sequencing adapter, respectively, the first sequencing adapter being connected with one end of the insert and the second sequencing adapter being connected with the other end of the insert; performing a first extension treatment on the nucleic acid molecule to be detected by using a first dNTP mixture and a sequencing primer, the sequencing primer being paired with one of the first sequencing adapter and the second sequencing adapter, and the sequencing primer extending to upstream of the predetermined region; and performing a second extension treatment on a product of the first extension treatment by using a second dNTP mixture, the nucleic acid sequence of the predetermined region being determined in the second extension treatment. The first dNTP mixture includes dATP, dTTP, dGTP, and dCTP, at least one of the dATP, dTTP, dGTP, and dCTP carrying a polymerase reaction blocking group; and the second dNTP mixture comprises dATP, dTTP, dGTP, and dCTP, each of the dATP, dTTP, dGTP, and dCTP carrying a polymerase reaction blocking group, and at least one of the dATP, dTTP, dGTP, and dCTP carrying a detectable group. The "read length of the sequencer" refers to the maximum length of the nucleic acid sequence that can be accurately read by a sequencer. The length of the insert greater than the read length of the sequencer means that the length of the insert is at least 400 bp, at least 500 bp, or at least 600 bp.

According to the embodiments of the present disclosure, the above method for determining a nucleic acid sequence of a predetermined region of a nucleic acid molecule to be detected can further include the following technical features:

In some embodiment of the present disclosure, the first extension treatment includes: step 1 of annealing the nucleic acid molecule to be detected and the sequencing primer to form an initial duplex, the initial duplex consisting of the nucleic acid molecule to be detected and the sequencing primer; step 2 of incorporating, by using the sequencing primer in the initial duplex as a first initial growth nucleic acid strand, at least one dNTP of the first dNTP mixture to a 3'-end of the initial growth nucleic acid strand under catalysis of a polymerase to elongate at least one base at the 3'-end of the initial growth nucleic acid strand, and forming a first duplex product; step 3 of cleaving the first duplex product to remove the polymerase reaction blocking group on the first duplex product; and step 4 of repeating the steps 2 to 3 until the sequencing primer extends to a predetermined position upstream of the predetermined region.

In some embodiments of the present disclosure, each of the dATP, dTTP, dGTP, and dCTP in the first dNTP mixture carries the polymerase reaction blocking group. Since each of the dATP, dTTP, dGTP, and dCTP in the first dNTP mixture carries the polymerase reaction blocking group, the cleavage can be performed when one base is elongated, so as to ensure the base extend to the predetermined position.

In some embodiments of the present disclosure, only one of the dATP, dTTP, dGTP, and dCTP in the first dNTP mixture carries polymerase reaction blocking group.

In some embodiments of the present disclosure, at most three of the dATP, dTTP, dGTP, and dCTP in the first dNTP mixture carry the polymerase reaction blocking group. Since at most three of dATP, dTTP, dGTP, and dCTP carry the polymerase reaction blocking group, the extension accuracy and the extension efficiency can be guaranteed at the same time.

In some embodiments of the present disclosure, none of the dATP, dTTP, dGTP, and dCTP in the first dNTP mixture carries the detectable group.

In some embodiments of the present disclosure, in the step 4, the predetermined position is located within 1-100 bp upstream of the predetermined region.

In some embodiments of the present disclosure, the product of the first extension treatment has a length of at least 200 bp, and preferably 200 bp to 600 bp.

In some embodiments of the present disclosure, in the step (4), a distance between the predetermined position and an end of downstream of the predetermined region is smaller than or equal to 400 bp, and preferably smaller than or equal to 300 bp.

In some embodiments of the present disclosure, the second extension treatment includes: step a of incorporating, by using the product of the first extension treatment as a starting point, one dNTP of the second dNTP mixture paired to the 3'-end of the product of the first extension treatment under the catalysis of a polymerase to elongate a new base at the 3'-end of the product of the first extension treatment, forming a second duplex product, and determining a type of the new base by detecting the detectable group of the second duplex product; step b of cleaving the second product duplex to remove the polymerase reaction blocking group and the detectable group on the second duplex product; and step c of repeating the steps a to b until types of bases of the predetermined region are partially determined.

In some embodiments of the present disclosure, the detectable group is a fluorescent group or a phosphorescent group.

In some embodiments of the present disclosure, the dATP, dTTP, dGTP, and dCTP all carry different detectable groups.

According to a second aspect of the present disclosure, the present disclosure provides a dNTP mixture for use in the sequencing method according to any one of the embodiments in the first aspect of the present disclosure.

According to a third aspect of the present disclosure, the present disclosure provides a nucleic acid molecule for nucleic acid sequencing, including: an insert having a length of which is at least 500 bp, preferably at least 800 bp, for example, 1000-1200 bp; a first sequencing adapter connected to one end of the insert; and a second sequencing adapter connected to the other end of the insert. By using the nucleic acid molecule for nucleic acid sequencing provided by the present disclosure, the sequence of long inserts can be determined, thereby ensuring the accuracy and rapidity of sequencing.

According to an embodiment of the present disclosure, the nucleic acid molecule for nucleic acid sequencing further includes: a tag sequence arranged in the first sequencing adapter or the second sequencing adapter.

According to a fourth aspect of the present disclosure, the present disclosure provides a sequencing library containing the insert nucleic acid molecule according to the first aspect of the present disclosure. The sequencing library composed of the nucleic acid molecules described in the first aspect of the present disclosure can realize the determination of the nucleic acid sequence of the insert in the nucleic acid molecule, or the determination of the nucleic acid sequence of a certain predetermined region of the insert nucleic acid molecule.

According to a fifth aspect of the present disclosure, the present disclosure provides a sequencing chip, and the sequencing chip carries the insert nucleic acid molecule according to the first aspect of the present disclosure. The sequencing chip carries nucleic acid molecules for nucleic acid sequencing, which can be directly used for sequencing nucleic acid molecules, so that sequencing can be realized conveniently and quickly.

According to a sixth aspect of the present disclosure, the present disclosure provides a method for determining a nucleic acid sequence of a nucleic acid molecule to be detected. An insert of the nucleic acid molecule to be detected is at least 700 bp and is divided into a first region, a second region, and a third region. The first region, the second region, and the third region are sequentially connected, and the sizes of the first region, the second region, and the third region are approximately the same. The method includes step 1' of determining, with the method according to any one of the embodiments of the first aspect of the present disclosure, nucleic acid sequences of the first region, the second region, and the third region of the nucleic acid molecule to be detected, respectively; and step 2' of determining the nucleic acid sequence of the nucleic acid molecule based on a result of the step 1'.

The sentence of "the sizes of the first region, the second region, and the third region are approximately the same" means that the sizes of the first region, the second region, and the third region are not required to be absolutely identical, but can be averaged as far as possible according to the sizes of the inserts. For example, the fragment size of each region can differ by 10 bp, 20 bp, 30 bp, 40 bp, 50 bp, or even 80 bp, 100 bp, etc. Of course, the sizes of the first region, the second region, and the third region are not all the same. For example, the size of the first region can be 200 bp, the size of the second region can be 300 bp, and the size of the third region can be 300 bp. In this text, "one time of sequencing" or "one round of sequencing" refers to one operation in a mixed system and environment. Following the first time of sequencing or the first round of sequencing, the second time of sequencing or the second round of sequencing means another operation, and the mixed system and environment corresponding to this operation are not necessarily the same as or different from the first sequencing or the first sequencing. The sizes of the first region, the second region and the third region are approximately the same to ensure the efficiency of each sequencing or each round of sequencing as much as possible, avoiding the situation that sequencing resources are wasted because the fragments of a certain region are too large or too small.

For example, when the insert of the nucleic acid molecule to be detected is 700 bp, the insert can be roughly divided into three regions on average, or it can be adjusted appropriately, for example, the first region is about 250 bp, the second region is about 250 bp, and the third region is about 200 bp. Then, the nucleic acid sequences of the first region, the second region, and the third region are determined respectively, and the sequencing sequence of the insert is obtained by sequence splicing.

In some embodiments of the present disclosure, the above method for determining the nucleic acid sequence of the nucleic acid molecule to be detected may further include the following technical features.

In some embodiments of the present disclosure, the insert of the nucleic acid molecule to be detected is about 1000 bp. A distance between a starting position of the first region and an end upstream of the insert is at least 600 bp, for example 660 bp; a distance between a starting position of the second region and the end upstream of the insert is at least 300 bp, for example 330 bp; and a starting position of the third region is the end upstream of the insert. The sentence of "the insert is about 1000 bp" means that the size of the insert is not absolutely required to be 1000 bp, which can deviate from 1000 bp, for example, it can deviate from 1000 bp by 10 bp, 20 bp, 30 bp, 40 bp, 50 bp, even 80 bp, 100 bp, etc.

In some embodiments of the present disclosure, the step 1' further includes: step a of pairing a repressor primer with a part of the nucleic acid molecule to be detected, and determining, with the method according to any one of the embodiments in the first aspect of the present disclosure, the nucleic acid sequence of the first region of the nucleic acid molecule to be detected, wherein the repressor primer has the same nucleic acid sequence as the sequencing primer, and a 3'-end of the repressor primer is provided with a repressor group; step b of cleaving and removing the repressor group of a part of the repressor primer, and determining, with the method according to any one of the embodiments in the first aspect of the present disclosure the nucleic acid sequence of the second region of the nucleic acid molecule to be detected; and step c of cleaving and removing the repressor group of a part of the repressor primer, and determining, with the method according to any one of the embodiments in the first aspect of the present disclosure, the nucleic acid sequence of the third region of the nucleic acid molecule to be detected.

In some embodiments of the present disclosure, the repressor group of the repressor primer is cleaved and removed by an endonuclease.

In some embodiments of the present disclosure, the step 1' further includes: step a of determining, with the method according to any one of the embodiments in the first aspect of the present disclosure, the nucleic acid sequence of the first region of the nucleic acid molecule to be detected, and denaturing and eluting a product of the second extension treatment with an alkaline solution to obtain the nucleic acid molecule to be detected; step b of determining, with the method according to any one of the embodiments in the first aspect of the present disclosure, the nucleic acid sequence of the second region of the nucleic acid molecule to be detected, and denaturing and eluting the product of the second extension treatment with the alkaline solution to obtain the nucleic acid molecule to be detected; and step c of determining, with the method according to any one of the embodiments in the first aspect of the present disclosure, the nucleic acid sequence of the third region of the nucleic acid molecule to be detected.

In some embodiments of the present disclosure, the alkaline solution is a NaOH solution.

In some embodiments of the present disclosure, the nucleic acid sequence of the third region of the nucleic acid molecule to be detected is determined without performing the first extension treatment.

According to a seventh aspect of the present disclosure, the present disclosure provides a method for determining a nucleic acid sequence of a nucleic acid molecule to be detected. An insert of the nucleic acid molecule to be detected is at least 700 bp. The method includes:

step A of dividing the insert of the nucleic acid molecule to be detected into a plurality of regions, each of the plurality of regions smaller than or equal to 400 bp, preferably smaller than or equal to 300 bp, and determining, with the method according to any one of the embodiments in the fourth aspect of the present disclosure, a nucleic acid sequence of each of the plurality of regions of the nucleic acid molecule to be detected; and step B of determining the nucleic acid sequence of the nucleic acid molecule based on a result of the step A.

The method provided by the present disclosure has the following beneficial effects. With the sequencing method provided by the present disclosure, the nucleic acid sequence of a long fragment or a predetermined region in the long fragment can be determined on the basis of low-cost sequencing with high accuracy.

Additional aspects and advantages of the present disclosure will be set forth in part or become clear in the description which follows, or may be learned by practice of the present disclosure.

BRIEF DESCRIPTION OF DRAWINGS

The above and/or additional aspects and advantages of the present disclosure will become apparent and easily understood from the description of embodiments in conjunction with the following drawings, in which.

DESCRIPTION OF EMBODIMENTS

Embodiments of the present disclosure are described in detail below, examples of which are shown in the accompanying drawings. The embodiments described below with reference to the drawings are illustrative and are intended to explain the present disclosure, but they should not be understood as limitations of the present disclosure. In the description of the present disclosure, when the nucleic acid molecules are "connected" and "linked", it means that two nucleic acid molecules are connected through 3',5' phosphodiester bond.

Nucleic Acid Molecules for Nucleic Acid Sequencing

The present disclosure provides a nucleic acid molecule for nucleic acid sequencing. The nucleic acid includes an insert, a first sequencing adapter, and a second sequencing adapter. The insert has a length of at least 500 bp, optionally at least 800 bp, for example, 1000 to 1200 bp. The first sequencing adapter is connected with one end of the insert, and the second sequencing adapter is connected to the other end of the insert.

Figure 1:
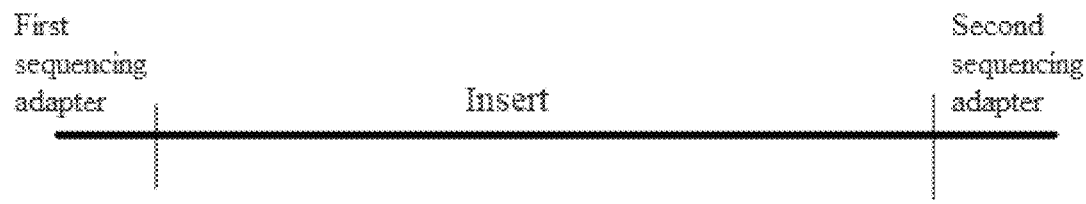
FIG. 1 is a schematic diagram of a nucleic acid molecule for nucleic acid sequencing according to an embodiment of the present disclosure.

According to an embodiment of the present disclosure, FIG. 1 illustrates a nucleic acid molecule used for nucleic acid sequencing, in which a first sequencing adapter is connected to a 5'-end of an insert, and a second sequencing adapter is connected to an 3'-end of the insert. According to an embodiment of the present disclosure, the positions of the first sequencing adapter and the second sequencing adapter can also be interchanged, that is, the first sequencing adapter can be connected to the 3'-end of the insert, and the second sequencing adapter is connected to the 5'-end of the insert.

Figure 2:
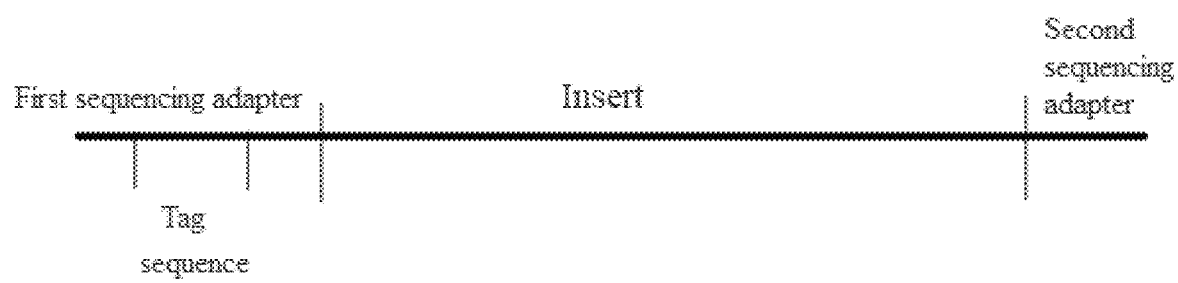
FIG. 2 is a schematic diagram of a nucleic acid molecule for nucleic acid sequencing according to an embodiment of the present disclosure.

The nucleic acid molecule used for nucleic acid sequencing may also include a tag sequence, such as a barcode sequence. The barcode sequence is disposed in the first sequencing adapter or the second sequencing adapter. As shown in FIG. 2, the tag sequence is provided in the first sequencing adapter. The tag sequences are configured to distinguish different biological samples. In the process of sequencing using the ILLUMINA® sequencing platform, the tag sequence and insert in the nucleic acid molecules are determined respectively. Therefore, the tag sequence can be provided in the first sequencing adapter or the second sequencing adapter, away from the insert. The tag sequence and insert are sequenced by using a sequencing primer.

Based on the nucleic acid molecule for nucleic acid sequencing as described above, the present disclosure also provides a sequencing library containing the above nucleic acid molecules used for nucleic acid sequencing. The sequencing library composed of the above-mentioned nucleic acid molecules for nucleic acid sequencing can realize the determination of nucleic acid sequences of the inserts in nucleic acid molecules or the determination of nucleic acid sequences of predetermined regions of the inserts in nucleic acid molecules. For example, the inserts in nucleic acid molecules can be sequenced by means of the ILLUMINA® HISEQ® 2500 sequencing platform, in which the first sequencing adapter and the second sequencing adapter can contain universal adapters P5 adapter and P7, respectively. The P5 adapter and P7 adapter, as the anchor sequences of the ILLUMINA® HISEQ® 2500 sequencing platform, can anchor inserts to a sequencing chip.

As an example, the ILLUMINA® HISEQ® 2000 or ILLUMINA® HISEQ® 2500 sequencing platform is a sequencing platform based on SBS technology. The bridge PCR reaction on the Flowcell can be performed by using single molecule array, and only one base can be synthesized at a time using reversible blocking technology; and the fluorescent group can be labeled on the base, and then the fluorescent group is excited by the corresponding laser and the excitation light can be captured for reading the base information. Similarly, the sequencing platforms that employ reversible blocking technology can construct a library and sequence a long nucleic acid according to the method of the present disclosure. For example, the cBot sequencing platform of ILLUMINA® can also be used. Those skilled in the art can select corresponding universal adapters according to different sequencing platforms to meet the requirements of library construction.

Based on the nucleic acid molecules for nucleic acid sequencing, the present disclosure also provides a sequencing chip carrying the nucleic acid molecules used for nucleic acid sequencing. The sequencing chip can carry the nucleic acid molecules used for nucleic acid sequencing by pairing the nucleic acid molecules for nucleic acid sequencing with complementary sequences of adapters on the sequencing chip. Then, the nucleic acid molecules can be sequenced by means of sequencing platform.

Method for Determining a Nucleic Acid Sequence of a Predetermined Region of a Nucleic Acid Molecule to be Detected According to another aspect of the present disclosure, for the above-described nucleic acid molecules for nucleic acid sequencing, a nucleic acid sequence in a predetermined region of the nucleic acid molecule can be determined by the following method. The method includes the following steps:

(1) performing a first extension treatment on the nucleic acid molecule to be detected by using a first dNTP mixture and a sequencing primer, wherein the sequencing primer is paired with one of the first sequencing adapter and the second sequencing adapter, and the sequencing primer extends to upstream of the predetermined region; and wherein the first dNTP mixture includes dATP, dTTP, dGTP, and dCTP, and at least one of dATP, dTTP, dGTP, and dCTP carries a polymerase reaction blocking group; and (2) performing a second extension treatment, by using a second dNTP mixture, on a product of the first extension treatment, wherein the nucleic acid sequence of the predetermined region is determined in the second extension treatment, the second dNTP mixture includes dATP, dTTP, dGTP, and dCTP that all carry polymerase reaction blocking groups, and at least one of dATP, dTTP, dGTP, and dCTP carries a detectable group.

The first dNTP mixture includes dATP, dTTP, dGTP, and dCTP, and at least one of dATP, dTTP, dGTP, and dCTP carries a polymerase reaction blocking group. The first dNTP mixture and a sequencing primer are mixed with the nucleic acid molecule to be detected, the sequencing primer can be paired with the first sequencing adapter or the second sequencing adapter of the nucleic acid molecule to be detected, and then under the action of polymerase and the dNTP mixture, the nucleic acid molecule to be detected is used as a template, and polymerization is carried out along the sequencing primer until the sequencing primer extends to upstream of a predetermined region of the nucleic acid molecule to be detected. The polymerase reaction blocking group is a group capable of blocking the polymerization reaction of the corresponding deoxynucleotide, for example, an azide group, phosphate ester, ethylene hydride; or a blocking group based on a disulfide bond. For example, dGTP may carry the polymerase reaction blocking group, and when the dGTP undergoes polymerization, the polymerization can be continued only when the polymerase reaction blocking group carried by the dGTP is cleaved. Based on the number of the cleavages, it can be determined that the sequencing primer extends to upstream of the predetermined region of the nucleic acid molecule to be detected.

According to another embodiment of the present disclosure, only one of dATP, dTTP, dGTP, and dCTP in the first dNTP mixture carries the polymerase reaction blocking group. In this way, the sequencing primer can rapidly extend to upstream of the predetermined region of the nucleic acid molecule to be detected.

According to another embodiment of the present disclosure, each of the dATP, dTTP, dGTP, and dCTP in the first dNTP mixture carries the polymerase reaction blocking groups.

According to a specific embodiment of the present disclosure, at most three of dATP, dTTP, dGTP, and dCTP in the first dNTP mixture carry the polymerase reaction blocking group. In this way, the sequencing primer can more accurately extend to upstream of the predetermined region of the nucleic acid molecule to be detected, and the blocking effect is better.

None of the dATP, dTTP, dGTP, and dCTP in the first dNTP mixture carries the detectable group.

According to a specific embodiment of the present disclosure, the first extension treatment includes the following steps: a step (1) of annealing the nucleic acid molecule to be detected and the sequencing primer to form an initial duplex, the initial duplex consisting of the nucleic acid molecule to be detected and the sequencing primer; a step (2) of using a sequencing primer in the initial duplex as a first initial growth nucleic acid strand, and incorporating at least one dNTP of the first dNTP mixture to a 3'-end of the initial growth nucleic acid strand under catalysis of a polymerase to elongate at least one base at the 3'-end of the initial growth nucleic acid strand, and forming a first product duplex; a step (3) of cleaving the first product duplex to remove the polymerase reaction blocking group on the first product duplex; and a step (4) of repeating the steps (2) to (3) until the sequencing primer extends to a predetermined position upstream of the predetermined region. In this way, the sequencing primer can extend to the predetermined position upstream of the predetermined region.

According to a specific embodiment of the present disclosure, the predetermined position may be located within 1-100 bp upstream of the predetermined region, for example, 1-80 bp, 1-50 bp, 1-30 bp, or 1-20 bp upstream of the predetermined region.

According to another embodiment of the present disclosure, a distance between the predetermined position and an end of downstream of the predetermined region is smaller than or equal to 400 bp, preferably smaller than or equal to 300 bp, or smaller than or equal to 200 bp. After the first extension treatment, the sequencing primer extends to the predetermined position upstream of the predetermined region, and the distance between the predetermined position and the end of downstream of the predetermined region is smaller than or equal to 400 bp, preferably smaller than or equal to 300 bp, or smaller than or equal to 200 bp, thereby sequencing the predetermined region at a time by means of the sequencing platform.

For the product obtained after the first extension treatment, i.e., the product obtained after the sequencing primer extends to upstream of the predetermined region, the second dNTP mixture is mixed with the product obtained after the first extension treatment for the second extension treatment. The second dNTP mixture includes dATP, dTTP, dGTP, and dCTP, and each of the dATP, dTTP, dGTP, and dCTP carries a polymerase reaction blocking group, and at least one of the dATP, dTTP, dGTP, and dCTP carries a detectable group. In the extension treatment, the type of each base can be accurately determined by using the detectable group and the polymerase reaction blocking group.

According to a specific embodiment of the present disclosure, the second extension treatment includes: a step (a) of using the product of the first extension treatment as a starting point, under the catalysis of a polymerase, incorporating one of the second dNTP mixture into the 3'-end of the product of the first extension treatment to elongate a new base at the 3'-end of the product of the first extension treatment, forming a second product duplex, and determining a type of the new base by detecting the detectable group of the second product duplex; a step (b) of cleaving the second product duplex to remove the polymerase reaction blocking group and the detectable group on the second product duplex; and a step (c) of repeating the steps (a) to (b) until at least part of base types of the predetermined region is determined.

According to some embodiments of the present disclosure, the detectable group may be a fluorescent group or a phosphorescent group. The dATP, dTTP, dGTP, and dCTP carry different detectable groups, respectively. The fluorescent group includes, but is not limited to, AF532, IF700, Cy5 or ROX, and the phosphorescent group includes, but is not limited to, zinc sulfide, strontium aluminate or calcium sulfide.

Based on the above method for determining the nucleic acid sequence of the predetermined region of the nucleic acid molecule to be detected, the nucleic acid sequence of the predetermined region of the nucleic acid molecule to be detected can be accurately determined. At the same time, with the help of this method, the nucleic acid sequence of the long insert can be accurately determined. For example, the nucleic acid molecules having a length of more than 700 bp, more than 800 bp and more than 1000 bp can be sequenced. For the sequencing of the long-fragment nucleic acid molecule, different regions of the long-fragment nucleic acid molecule can be sequenced, respectively, depending upon the length of the long-fragment nucleic acid molecule. That is, the long-fragment nucleic acid molecule is sequenced by segmental sequencing. For example, when the length of the long-fragment nucleic acid molecule is about 1000 bp, only about 330 bp from the terminal (i.e., the 3'-end) of the nucleic acid molecule to be detected is sequenced in the first round of sequencing, then only a fragment of about 330 bp in the middle of the nucleic acid molecule to be detected is sequenced in the second round of sequencing, only about 330 bp from the terminal (i.e., the 5'-end) of the nucleic acid molecule to be detected is sequenced in the third round of sequencing, and the nucleic acid sequence of the long-fragment insertion fragment can be accurately determined by sequence splicing.

Figure 3:
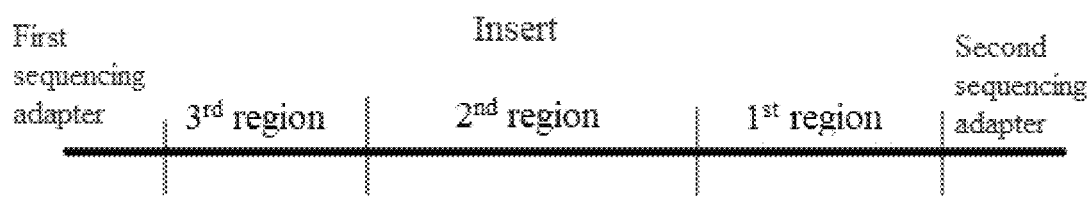
FIG. 3 is a schematic diagram of a regional determination of a nucleic acid molecule to be detected in a method for determining the nucleic acid sequence of the nucleic acid molecule to be detected according to an embodiment of the present disclosure.

Therefore, according to another aspect of the present disclosure, the present disclosure provides a method for determining the nucleic acid sequence of a nucleic acid molecule to be detected, in which the insert of the nucleic acid molecule to be detected is at least 700 bp, and the insert is divided into a first region, a second region and a third region, and the sizes of the first region, the second region and the third region are approximately the same. The method comprises: a step (1') of determining, with above method for determining a nucleic acid sequence of a predetermined region of a nucleic acid molecule to be detected, nucleic acid sequences of the first region, second region, and third region of the nucleic acid molecule to be detected, respectively; and a step (2') of determining the nucleic acid sequence of the nucleic acid molecule based on a result of the step (1'). When the size of the insert is about 1000 bp, as shown in FIG. 3, a distance between a starting position of the first region and an end upstream of the insert is at least 600 bp, for example 660 bp; a distance between a starting position of the second region and the end upstream of the insert is at least 300 bp, for example 330 bp; and a starting position of the third region is the end upstream of the insert. In this way, the sequence of the insert of the long fragment can be determined through the three determinations.

In the above, the nucleic acid sequences of different regions of the nucleic acid molecule to be detected can be determined, and the nucleic acid molecule containing long inserts can be determined by segmental sequencing. Of course, the nucleic acid sequence of the third region can be determined without performing the first extension treatment.

In at least some embodiments of the present disclosure, the step (1') further includes the following steps: (a) pairing a repressor primer with a part of the nucleic acid molecule to be detected, and determining, with the method for determining the nucleic acid sequence of a predetermined region of the nucleic acid molecule to be detected, the nucleic acid sequence of the first region of the nucleic acid molecule to be detected, wherein the repressor primer has the same nucleic acid sequence as the sequencing primer, and a 3'-end of the repressor primer is provided with a repressor group; (b) cleaving and removing a part of the repressor group of the repressor primer, and determining, with the above method for determining the nucleic acid sequence of a predetermined region of the nucleic acid molecule to be detected, the nucleic acid sequence of the second region of the nucleic acid molecule to be detected; and (c) cleaving and removing a part of the repressor group of the repressor primer, and determining, with the above method for determining the nucleic acid sequence of a predetermined region of the nucleic acid molecule to be detected, the nucleic acid sequence of the third region of the nucleic acid molecule to be detected.

By adjusting a ratio of the repressor primer to the normal sequencing primer, the repressor primer is paired with a part of the nucleic acid molecule to be detected, so as to determine the nucleic acid sequence in the first region in the first round of sequencing. Then, by removing part of the repressor groups, in the second round of sequencing, the sequence of the second region on the nucleic acid molecule that is complementary to these removed repressor groups is determined. In the same way, the sequence of different regions of the nucleic acid molecule can be individually determined.

In at least some embodiments, after the nucleic acid sequences of the first region and the second region are determined, after end-capping with ddNTP, the nucleic acid sequence of the next region is determined. After the nucleic acid sequence of one region of the nucleic acid molecule to be detected is determined, ddNTP can be used for end capping, so as to avoid the signal interference to the sequencing of the next sequence when the next sequence is sequenced in the next sequence. As an example, in one round of sequencing when the first region of the nucleic acid molecule to be detected is sequenced, the first region of the nucleic acid molecule to be detected is sequenced with the above method for determining the nucleic acid sequence of the predetermined region of the nucleic acid molecule to be detected. And when the product obtained after the first extension treatment is subjected to the second extension treatment by using the second dNTP mixture, after the polymerase reaction blocking group of the last dNTP is cleaved and the corresponding base is determined, the product is end-capped with ddNTP. Then the next round of sequencing is started.

In practice, the mixed primer system and Primer Walking (PW) technology can be used to realize sequencing of different regions, i.e., segmental sequencing. The mixed primer system is a mixture containing standard sequencing primers and repressor primers, which can ensure that only about one third of DNA strands in the DNA cluster on Flowcell can be sequenced in the first round of sequencing. The primer extension does not occur on the DNA strand that can complementarily pair with the repressor primer in the mixture, and will occur in the second or third round of sequencing once the repressor group on the repressor primer is cleaved and removed. The nucleic acid sequence of the repressor primer is the same as that of the standard sequencing primer, and both of them can complementarily pair with the DNA strand. The difference therebetween is that the 3'-end of the repressor primer has a repressor group configured to inhibit the subsequent extension reaction. The repressor group can be an azide group, phosphate ester, ethylene hydride, or disulfide-based groups, as long as it can inhibit the extension reaction. When dNTP carries the polymerase reaction blocking group (azide group), the azide group cannot be used as the repressor group of the repressor primer. Otherwise, the inhibition effect of the repressor primer will be eliminated when the polymerase reaction blocking group carried by dNTP is cleaved and removed.

As an example, the insert having a length about 1000 bp, in the primer walking (PW) stage of the first round of sequencing, the mixture of dNTP mainly consists of the following components: dATP, dTTP, dCTP, and dGTP that have a polymerase reaction blocking group (azide group). After polymerization, the azido group carried by dGTP is removed to ensure the subsequent polymerization. After N cycles of polymerization/cleaving, the length of the newly synthesized chain will reach ~660 bp. Taking this as a node, the dNTP mixture having a fluorescent group is added for routine single-ended sequencing to obtain the gene sequence of 340 bp at the end of the insert.

Before the start of the next round of sequencing, the repressor groups of some repressor primers are cleaved. The endonuclease Endo IV can be used to cleave the repressor group. In the subsequent PW stage, the number of cycles of polymerization/cleavage reaction is (approximately) halved, and the length of the newly synthesized chain reaches about 330 bp. Taking this as a node, the dNTP mixture having a fluorescent group is added for routine single-ended sequencing to obtain the gene sequence of about 330 bp in the middle end of the DNA insert.

Before the start of the third round of sequencing, the repressor groups carried by the remaining repressor primers are cleaved. Then, the mixture of dNTPs having a fluorescent group is added for routine single-ended sequencing of the remaining DNA strands in the same DNA cluster to obtain the gene sequence of about 330 bp at the front end of the DNA insert. Finally, the DNA sequences obtained by three rounds of sequencing are analyzed and spliced into a complete 1000 bp DNA insert.

In at least some embodiments, the step (1') further comprises: (a) determining, with the above method for determining a nucleic acid sequence of a predetermined region of a nucleic acid molecule to be detected, the nucleic acid sequence of the first region of the nucleic acid molecule to be detected, and denaturing and eluting the product of the second extension treatment with an alkaline solution to obtain the nucleic acid molecule to be detected; (b) determining, with the above method for determining a nucleic acid sequence of a predetermined region of a nucleic acid molecule to be detected, the nucleic acid sequence of the second region of the nucleic acid molecule to be detected, and denaturing and eluting the product of the second extension treatment with an alkaline solution to obtain the nucleic acid molecule to be detected; and (c) determining, with the above method for determining a nucleic acid sequence of a predetermined region of a nucleic acid molecule to be detected, the nucleic acid sequence of the third region of the nucleic acid molecule to be detected.

In practice, the primer walking (PW) technology and new synthetic strand elution technology can be used to fragmentally sequence the different regions (i.e., segmental sequencing).

Taking the insert of 1000 bp as an example, in the first round of sequencing, a sufficient amount of standard sequencing primers is complementarily hybridized with primer binding sites on the DNA strands to be detected, and then a dNTP mixture consisting of dATP, dTTP, dCTP, and repressor dGTP is added. After the polymerization reaction, the repressor group carried by dGTP is cleaved to ensure the subsequent polymerization reaction. After N cycles of polymerization/cleavage (PW), the length of the newly synthesized chain can reach ~660 bp. Taking this as a node, the mixture of dNTPs having the fluorescent group is added for routine single-ended sequencing to obtain the gene sequence of 340 bp at the end of the insert. After the first round of sequencing, NaOH is used to unwind the double strands, and the newly synthesized strand is eluted from the chip. Before the start of the second round of sequencing, a sufficient amount of standard sequencing primers is complementarily hybridized with primer binding sites on the DNA strands to be detected, and then a dNTP mixture consisting of dATP, dTTP, dCTP, and repressor dGTP is added. After the polymerization reaction, the repressor group carried by dGTP is cleaved to ensure the subsequent polymerization reaction. After N cycles of polymerization/cleavage (i.e., PW), the length of the newly synthesized chain will reach ~330 bp. Taking this as a node, the mixture of dNTPs having a fluorescent group is added for routine single-ended sequencing, so as to obtain the gene sequence of 330 bp in the middle of the insert. After the second round of sequencing, NaOH is used to unwind the double strands, and the newly synthesized strand is eluted from the chip.

Before the start of the third round of sequencing, the standard sequencing primers are complementarily hybridized with the primer binding sites on the DNA strands to be detected, and then mixture of dNTPs having a fluorescence group is added to carry out routine single-ended sequencing on the remaining DNA strands in the same DNA cluster to obtain the gene sequence of about 330 bp at the front end of the DNA insert. Finally, the DNA sequences obtained by the three rounds of sequencing are analyzed and spliced into a complete 1000 bp DNA insert.

NaOH alkaline solution is used to denature and elute the double strand. When compared with denaturing by traditional annealing, it can prevent the stability of chemical bonds in double-stranded nucleic acid molecules from being influenced by long double strands and high annealing temperature.

Therefore, according to another aspect of the present disclosure, the present disclosure also provides a method for determining a nucleic acid sequence of a nucleic acid molecule to be detected, in which an insert of the nucleic acid molecule to be detected is at least 700 bp. The method includes: a step (A) of dividing the insert of the nucleic acid molecule to be detected into a plurality of regions, each of the plurality of regions smaller than or equal to 400 bp, preferably smaller than or equal to 300 bp, and determining, with the above method for determining a nucleic acid sequence of a nucleic acid molecule to be detected, a nucleic acid sequence of each of the plurality of regions of the nucleic acid molecule to be detected; and a step (B) of determining the nucleic acid sequence of the nucleic acid molecule based on a result of the step (A). In at least one embodiment, the length of the insert of the nucleic acid molecule to be detected is at most 1500 bp. When the insert of the nucleic acid molecule to be detected is too long, it may affect the accuracy of sequencing. The appropriate size of the insert is below 1500 bp. In at least some embodiments of the present disclosure, after the nucleic acid sequence of each one region is determined and end-capped with ddNTP, the nucleic acid sequence of the next region is determined, thereby avoiding the interference of detection signals during the determination of the nucleic acid sequences in different regions.

The solutions of the present disclosure will be explained with the following examples. Those skilled in the art will understand that the following examples are only used to illustrate the present disclosure, and should not be regarded as limitations of the scope of the present disclosure. If the specific technology or conditions are not indicated in the embodiments, it shall be carried out according to the technology or conditions described in the literatures in this field or according to the product instructions. The reagents or instruments used, without indication of the manufacturers, are conventional products that are commercially available.

Example 1

According to the gene sequencing method provided by the present disclosure, the single-ended sequencing of the gene can reach the read length of 1000 bp or more by using the ILLUMINA® HISEQ® 2500 sequencing platform.

Figure 4:
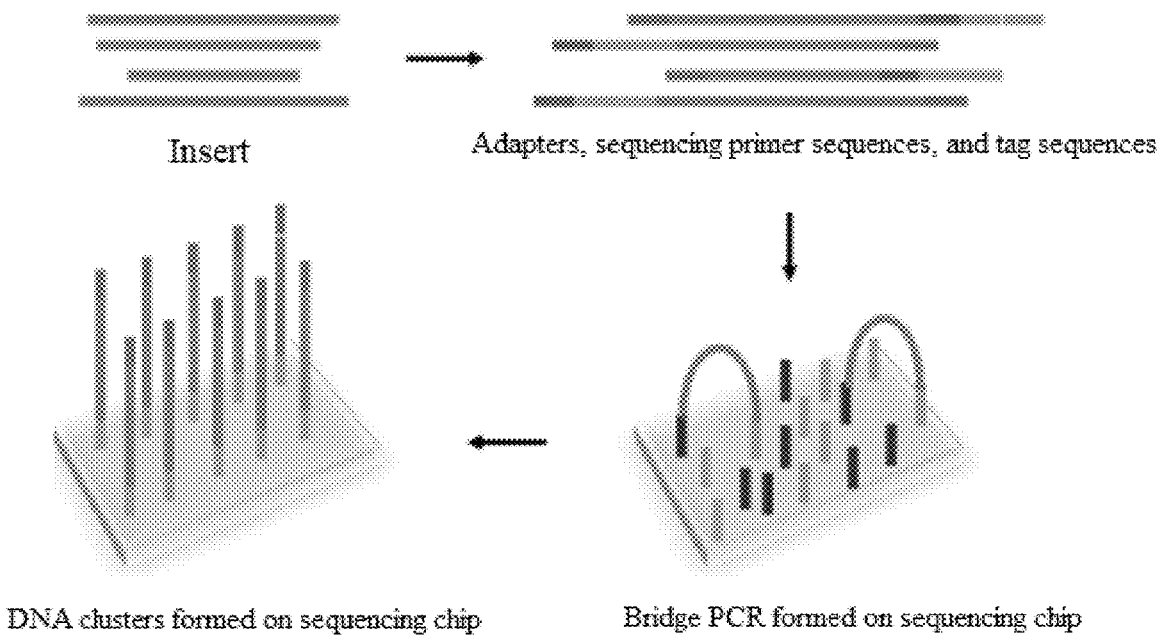
FIG. 4 is a schematic diagram of constructing a sequencing chip carrying an insert according to an embodiment of the present disclosure.

As shown in FIG. 4, a barcode sequence, a sequencing primer sequence, and a universal adapter P7 or P5 (as one adapter sequence) were ligated to one end of a single-stranded DNA fragment having a length of about 1000 bp, while P5 or P7 (as another adapter sequence) was directly ligated to the other end of the DNA insert to prepare a library. Two different oligonucleotide sequences, one of which is complementary to P5 (i.e., P5'), and the other one of which is consistent with P7 (i.e., P7), were randomly distributed on the sequencing chip Flowcell. The DNA fragments to be detected were complementarily hybridized with P5' sequence on the Flowcell via the adaptors P5 carried by themselves, and using the DNA fragment to be detected as a template, the complementary chain was elongated and has two ends, P5' and P7'. Then, the template strand was cleaved and eluted, and only the complementary strand was remained, while the P7' of the complementary strand was hybridized with the P7 on the Flowcell to synthesize the strand, that is, bridge PCR. Next, the synthesized double strand was denatured, then hybridized with the adapter on the Flowcell to complement each other, and extension, denaturing and hybridization were repeated for several cycles. After the bridge PCR was finished, the double strands were unwound using NaOH, and the connection between P5' and the strand was selectively cleaved by selectively cleaving 8-oxoguanine glycoside with Formamido pyrimidine glycosidase, and the strands connected with P7 were remained on Flowcell. At the same time, the free 3'-end was blocked by ddNTPs to prevent unnecessary DNA elongation. In this way, several relatively independent DNA clusters are synthesized on the chip Flowcell, and each DNA cluster consisted of thousands of copies of DNA strands carrying the same DNA insert.

Figure 5:
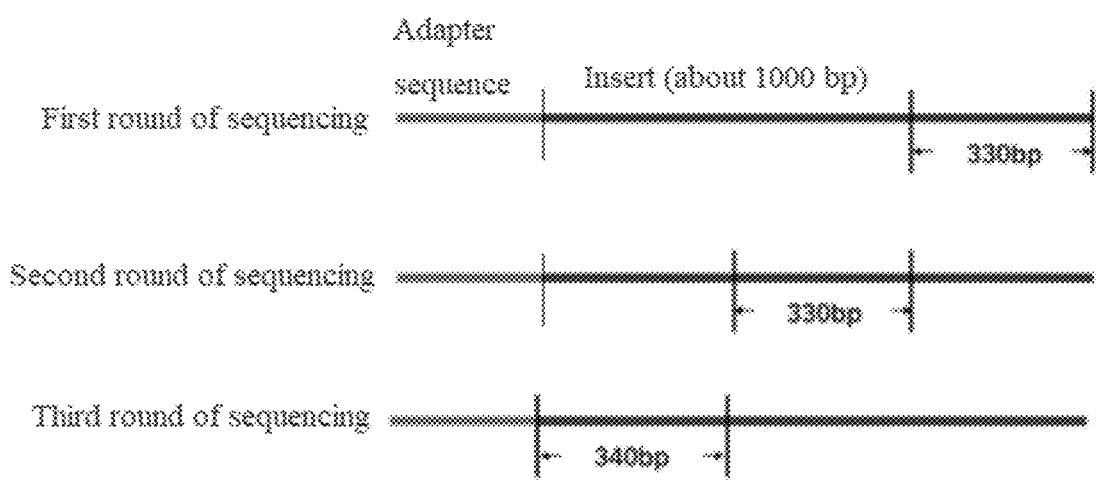
FIG. 5 is a schematic diagram of sequencing a long insert by three rounds of sequencing according to an embodiment of the present disclosure.

Then, as shown in FIG. 5, the long DNA library fragments were sequenced in segments, that is, only a fragment of 330 bp at the tail end of the DNA insert to be detected was sequenced in the first round of sequencing, a fragment of 330 bp in the middle of the DNA insert to be detected was sequenced in the subsequent second round of sequencing, and a fragment of 330 bp at the front end of the DNA insert to be detected was sequenced in the third round of sequencing. In this way, the experimental purpose of long read length was achieved indirectly through sequence splicing.

Figure 6:
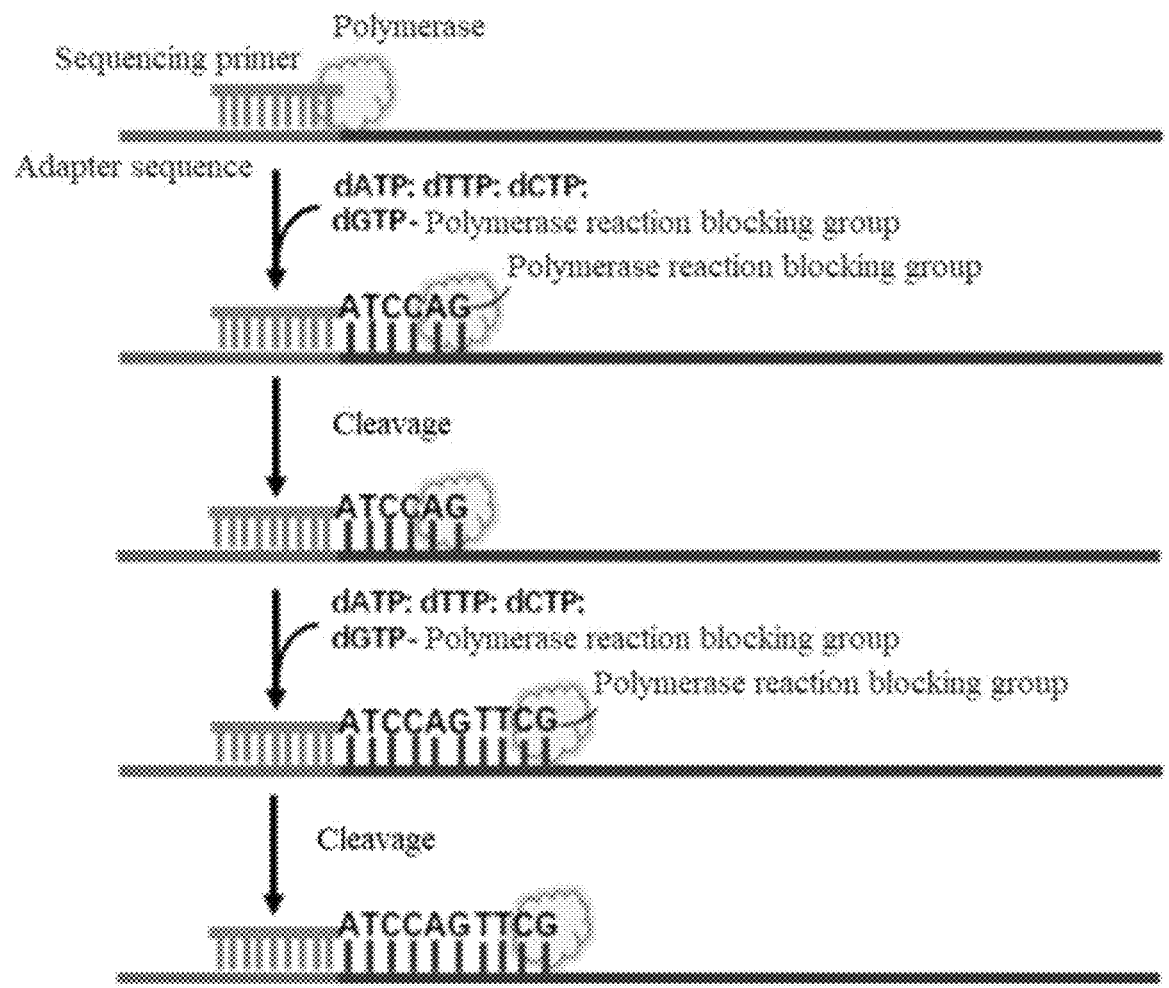
FIG. 6 is a schematic diagram of sequencing a long insert by three rounds of sequencing according to an embodiment of the present disclosure.
Figure 7:
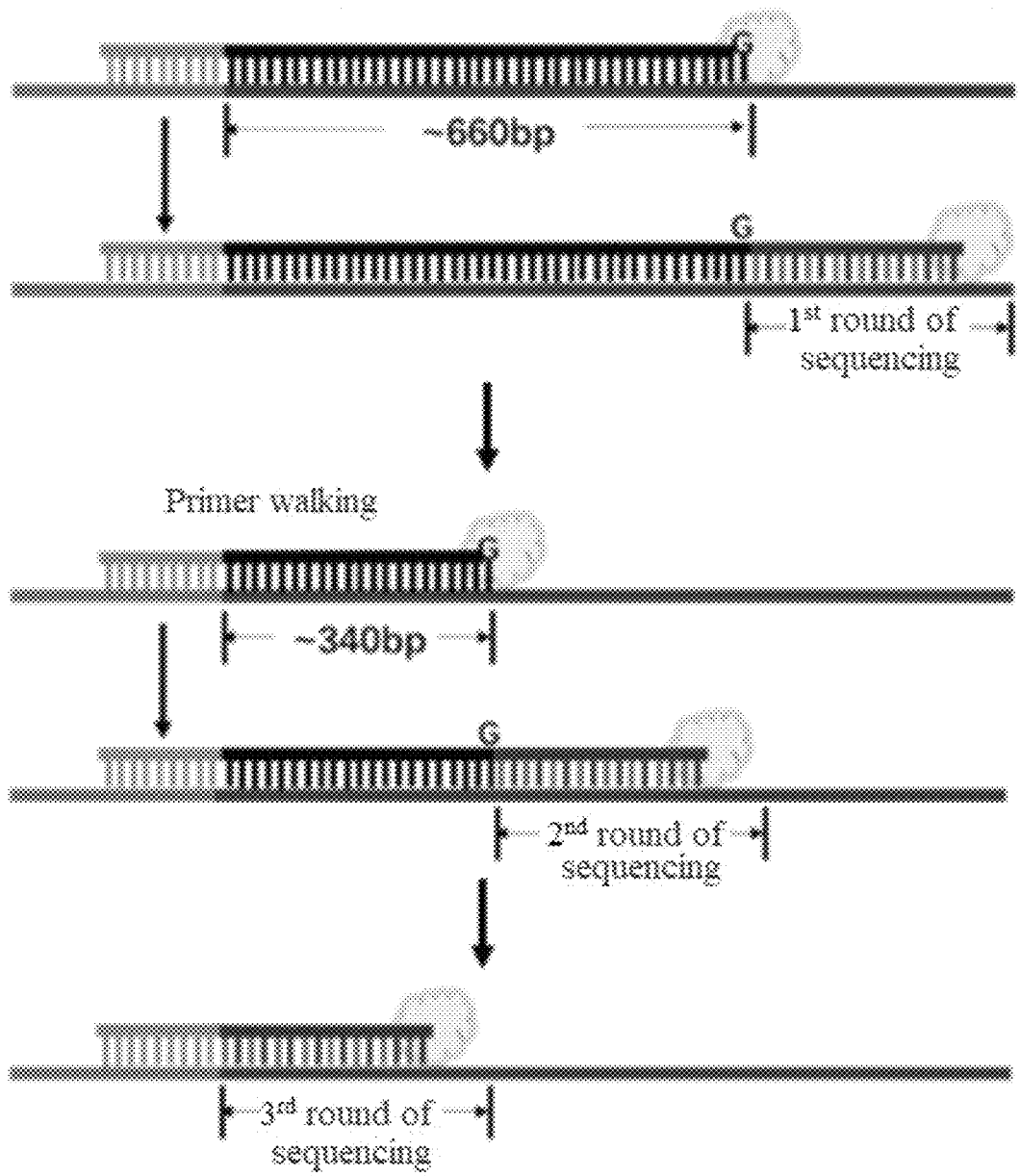
FIG. 7 is a schematic diagram sequencing a long insert by three rounds of sequencing according to an embodiment of the present disclosure.

The above-mentioned segmental sequencing can be realized by using mixed primer system and primer walking (PW) technology, as shown in FIG. 6 and FIG. 7.

The mixed primer system was a mixture of standard sequencing primers and repressor primers. This hybridization technology can ensure that only about one third of the DNA strands in the DNA cluster on Flowcell can be sequenced in the first round of sequencing. The DNA strand complementarily paired with the repressor primer in the mixture without initiating primer extension, and the DNA strand was elongated in the second or third sequencing after the repressor group on the repressor primer was cleaved. The nucleic acid sequence of the repressor primer was the same as that of the standard sequencing primer, and both of them could complementarily pair with the DNA strand. The difference therebetween was that the 3'-end of the repressor primer had phosphorylation modification for preventing the subsequent extension reaction.

In the primer walking (PW) stage of the first round of sequencing, the dNTP mixture mainly consisting of dATP, dTTP, DCTP, and dGTP that have a polymerase reaction blocking group (an azide group) was added. After polymerization, the azido group carried by dGTP was cleaved and removed to ensure the subsequent polymerization. After N cycles of polymerization/cleavage, the length of the newly synthesized chain reached ~660 bp. Taking this as a node, the mixture of dNTPs having a fluorescent group was added for routine single-ended sequencing to obtain the gene sequence of 340 bp at the end of the insert.

Before the start of the next round of sequencing, the repressor groups of some repressor primers were cleaved. The endonuclease Endo IV was used to cleave the repressor group. In the subsequent PW stage, the number of cycles of polymerization/cleavage reaction was (approximately) halved, and the length of the newly synthesized chain reached about 330 bp. Taking this as a node, the dNTP mixture having a fluorescent group was added for routine single-ended sequencing to obtain the gene sequence of about 330 bp in the middle of the DNA insert.

Before the start of the third round of sequencing, the repressor groups carried by the remaining repressor primers were cleaved. After that, the dNTP mixture having a fluorescent group was added for routine single-ended sequencing of the remaining DNA strand in the same DNA cluster to obtain the gene sequence of about 330 bp at the front end of the DNA insert.

Finally, the DNA sequences obtained by the three rounds of sequencing were analyzed and spliced into the complete 1000 bp DNA insert.

The accuracy of the above method was verified by measuring and analyzing the sequence of *Escherichia coli*. The specific materials, experimental steps, and experimental results are as follows:

1. Experimental Materials
   1). *Escherichia coli* single-stranded DNA template (with a length of about 1000 bases)
   2). Preparation of an AmpliSeq for Illumina library, barcode adapters, and matching products
   3). HiSeq SR cluster generation kit v4-cBot
   4). HiSeq SBS kit V4
   5). The sequence of the repressor primer was the same as that of standard sequencing primer, but it was phosphorylated at the 3'-end for elongation. The repressor primer was produced and provided by Sangon Biotech, Shanghai. The repressor primer sequence was 5'-GCGTAGCGCGGAACCATGGTTCCGCGC-TACGGCTCACAGAACGACATGGCTACGA TCCGACTT-3'P.
   6). Endonuclease 4, purchased from NEB.
2. Experimental Procedure
   1). According to the instructions of AmpliSeq for ILLUMINA® preparation library and labeling adapter kit, an amplicon library for an ILLUMINA® sequencer was prepared.
   2). According to the instructions of HiSeq SR cluster generation kit v4-cBot, the library prepared in the previous step was loaded on the Flowcell and isothermally amplified to generate clone clusters with about 1000 copies per cluster for sequencing on the HiSeq-supported system.
   3). The mixed primer system, i.e., the mixture of the standard sequencing primer and repressor primer, was complementarily hybridized with the primer binding site on the DNA strand on Flowcell.
   4). Sequencer startup: referring to the instruction manual of ILLUMINA® gene sequencer, the built-in control program (single-ended sequencing) corresponding to the sequencer was started.

5). Cleaning the instrument: the flow channels of the ILLUMINA® gene sequencer were cleaned with a cleaning chip. The specific refers to the instruction manual of the instrument.
6). PW reagent loading: the fluorescent dNTP mixture in HiSeq SBS kit V4 was replaced with the mixture of non-fluorescent dATP, dTTP, dCTP, and dGTP having an azide repressor group, and then the kit with the PW reagent was placed into the refrigerator of the sequencer.
7). Reagent preloading: reagent preloading was carried out according to the instruction manual of the ILLU-MINA® gene sequencer.
8). The chip to be detected (the chip prepared in the above step 2) was installed, followed by starting PW and performing 167 rounds (660 bp) of polymerization/ablation reaction.
9). After PW was completed, the reagent tank was taken out.
10) Loading of the sequencing reagent: the HiSeq SBS kit V4 was placed into the refrigerator of the sequencer.
11). Reagent preloading: reagent preloading was carried out according to the instruction manual of ILLU-MINA® of the gene sequencer.
12). Sequencing in the first round: a fragment of 330 bp at the tail end of the DNA insert in the segmental sequencing process was sequenced. At the end of the first sequencing, the newly synthesized DNA strands were blocked by the ddNTP mixture.
13). Restoration of the polymerization ability of part of the repressor sequencing primers: endonuclease IV (purchased from NEB) was diluted with a commercial buffer according to a ratio of 1:100, then introduced into the chip, and incubated at 37° C. for 5 minutes. Endonuclease IV was used to cleave the phosphate group at the 3'-end of some repressor primers to restore its growth and polymerization ability.
14). The above steps 6) and 7) were repeated in sequence, and the second round of PW began, and 84 rounds (about 340 bp) of polymerization/cleavage reaction were performed.
15). The above steps 9)-11) were repeated in sequence, and the second round of sequencing of the fragment 330 bp at the middle of the DNA insert in the segmental sequencing was carried out. At the end of this round of sequencing, the newly synthesized DNA strands were blocked by using the ddNTP mixture again.
16). Restoration of the polymerization ability of the remaining repressor sequencing primers: endonuclease 4 was used to cleave the phosphate group modified at the 3' growth end of the remaining repressor primers to restore their growth polymerization ability.
17). The above steps 10)-11) were repeated in sequence, and the final round of sequencing of the fragment of 330 bp at the front end of the DNA insert in the segmental sequencing flow was carried out.
18). The instrument was cleaned according to the instruction manual of the ILLUMINA® gene sequencer.
19). DNA sequences obtained by the three rounds of sequencing were analyzed and spliced into the complete 1000 bp DNA insert.

3. Experimental Results

Compared with the existing single-ended sequencing technology (i.e., sequencing an insert with a length of 400 bp in *Escherichia coli* by using the ILLUMINA® sequencing platform), the insert with a length of 400 bp corresponds to the first segment of the sequence and a part of the middle segment of the sequence of the segmental sequencing of the present disclosure. The comparison results are as follows:

TABLE 1

| | Sequencing results. | | | |
|---|---|---|---|---|
| | Single-ended sequencing 400bp | First round of sequencing in segmental sequencing (330bp) | Second round of sequencing in segmental sequencing (330bp) | Third round in segmental sequencing (340bp) |
| Q30% | 78.57 | 91.5 | 91.8 | 92.6 |
| ESR % | 87.84 | 88.37 | 89.02 | 89.75 |
| Mapping Rate % | 88.9 | 95.3 | 96.1 | 96.3 |
| Avg Error Rate % | 1.96 | 0.19 | 0.16 | 0.16 |

Figure 8:
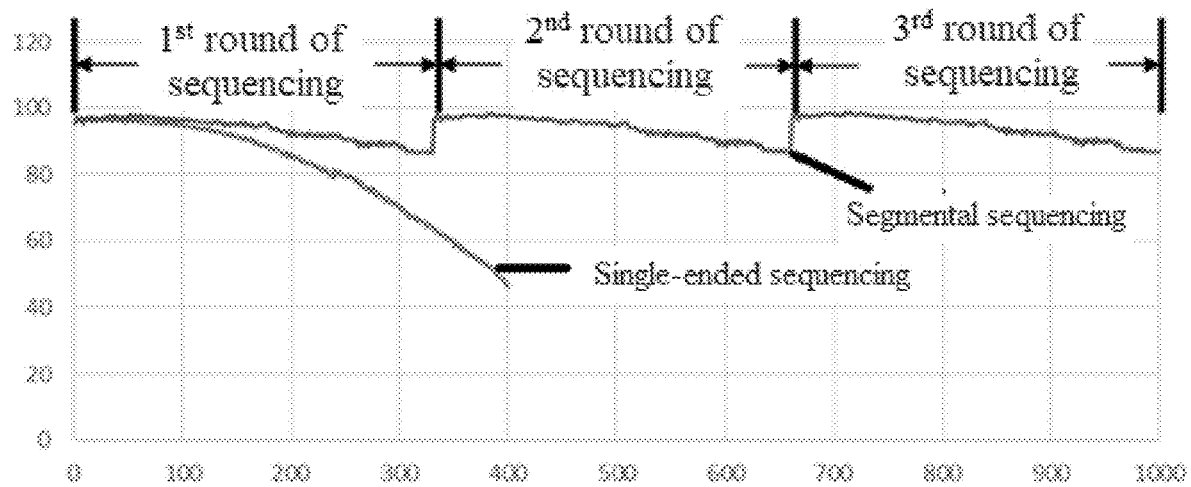
FIG. 8 is a schematic diagram of a sequencing mass ratio (Q30) distribution according to an embodiment of the present disclosure.

The result of Q30 is shown in FIG. 8. It can be seen from Table 1 and FIG. 8 that the performances of the segmental sequencing technology in terms of various important sequencing quality indicators, including Q30, ESR, mapping rate, and avg. error rate are obviously superior to the former and higher than the current requirements for sequencing quality, satisfying the requirements for reading long sequences. Q30 (Quality Proportion Distribution) in Table 1 represents the measured base quality, that is, the base occupancy rate with the error rate lower than 0.001 (the accuracy higher than 99.9%) by using basecall sequencing software. ESR (effective spot rate) is to exclude DNB which is not loaded or emits abnormal light, so as to ensure the accuracy of the results. The quality value of each base of each DNB is calculated to determine whether reads will be filtered because of its low quality. The larger the ESR value, the more qualified reads. Mapping rate represents a ratio of reads that can be accurately paired to the reference sequence to the total reads. The larger the mapping rate value, the larger the proportion of reads that can be accurately paired with the reference sequence. Average error rate (Avg Error Rate %) represents an error pairing ratio, which is the average value of error pairings at each point in the whole lane. The smaller the average error rate, the better the sequencing effect.

With the help of the ILLUMINA® sequencing platform, the inserts with the same size, for example, 400 bp, are sequenced, and the sequencing result obtained by the method provided by the prevent disclosure is more accurate. Without being limited by theory, the reason thereof can be speculated to be: 1) the dNTPs used in polymerization are different, i.e., the routine single-ended sequencing uses modified repressor dNTPs in each round of polymerization, while ¾ of the dNTPs are native in the new method, and the polymerization efficiency and accuracy of polymerase for modified and natural dNTPs may be different; and 2) base mismatch may accumulate along with primer extension, and the less repeated primer extension, the lower the probability of base mismatch. In the step of primer extension, the new method estimates that four bases can be polymerized in each round, which is four times that of the conventional single-ended sequencing method.

Example 2

Example 2 provides an approach for the above-mentioned segmental sequencing with primer walking (PW) technology and new synthetic strand elution technology, which was verified by measuring and analyzing the sequence of *Escherichia coli*.

In the first round of sequencing, sufficient standard sequencing primers were complementarily hybridized with primer binding sites on the DNA strands to be detected, and then a dNTP mixture consisting of dATP, dTTP, dCTP, and repressor dGTP was added. After the polymerization reaction, the repressor group carried by dGTP was cleaved through the cleavage reaction to ensure the subsequent polymerization reaction. After N cycles of polymerization/cleavage (i.e., PW), the length of the newly synthesized chain would reach ~660 bp. Taking this as a node, the dNTP mixture having a fluorescent group was added for routine single-ended sequencing to obtain the gene sequence of 340 bp at the tail end of the insert. After the first round of sequencing, NaOH was used to unwind the double strands, and the newly synthesized strands were eluted from the chip.

Before the start of the second round of sequencing, sufficient standard sequencing primers were complementarily hybridized with the primer binding sites on the DNA strand to be detected, and then a dNTP mixture consisting of dATP, dTTP, dCTP, and repressor dGTP was added. After the polymerization reaction, the repressor group carried by dGTP was cleaved through the cleavage reaction to ensure the subsequent polymerization reaction. After N cycles of polymerization/cleavage (i.e., PW), the length of the newly synthesized chain would reach ~330 bp. Taking this as a node, the dNTP mixture with a fluorescent group was added for routine single-ended sequencing, so as to obtain the gene sequence of 330 bp in the middle of the insert. After the second round of sequencing, NaOH was used to unwind the double strand, and the newly synthesized strands were eluted from the chip.

Before the start of the third round of sequencing, the standard sequencing primers were complementarily hybridized with the primer binding sites on the DNA strand to be detected, and then dNTP mixture having a fluorescence group was added to carry out routine single-ended sequencing on the remaining DNA strands in the same DNA cluster to obtain the gene sequence of about 330 bp at the front end of the DNA insert. Finally, the DNA sequences obtained by the three rounds of sequencing were analyzed and spliced into a complete 1000 bp DNA insert.

Specific experimental materials, implementation steps and experimental results are as follows:
1. Experimental Materials
   1). *Escherichia coli* single-stranded DNA template (with a length of about 1000 bases)
   2). Preparation of an AmpliSeq for ILLUMINA® library, barcode adapters, and matching products
   3). HiSeq SR cluster generation kit v4-cBot
   4). HiSeq SBS kit V4
2. Experimental Procedure
   1). According to the instructions of AmpliSeq for ILLUMINA® preparation library and labeling adapter kit, an amplicon library for an ILLUMINA® sequencer was prepared.
   2) According to the instructions of HiSeq SR cluster generation kit v4-cBot, the library prepared in the previous step was loaded on the Flowcell and isothermally amplified to generate clone clusters with about 1000 copies per cluster for sequencing on the HiSeq-supported system.
   3). The excessive standard sequencing primers were complementarily hybridized with the primer binding sites on DNA strand on the Flowcell.
   4) Sequencer startup: referring to the instruction manual of ILLUMINA® gene sequencer, the built-in control program (single-ended sequencing) corresponding to the sequencer was started.
   5). Cleaning the instrument: the flow channel of the ILLUMINA® gene sequencer was cleaned with a cleaning chip. Please refer to the instruction manual of the instrument for details.
   6). PW reagent loading: the fluorescent dNTP mixture in HiSeq SBS kit V4 was replaced with the mixture of non-fluorescent dATP, dTTP, dCTP, and dGTP with an azide repressor group, and then the kit with the PW reagent was placed into the refrigerator of the sequencer.
   7). Reagent preloading: reagent preloading was carried out according to the instruction manual of the ILLUMINA® gene sequencer.
   8). The chip to be detected (the chip prepared in the above step 2) was installed, followed by starting PW and performing 167 rounds (660 bp) of polymerization/ablation reaction.
   9). After PW was completed, the reagent tank was taken out.
   10) Loading of the sequencing reagent: the HiSeq SBS kit V4 was placed into the refrigerator of the sequencer.
   11). Reagent preloading: reagent preloading was carried out according to the instruction manual of ILLUMINA® of the gene sequencer.
   12). Sequencing in the first round: a fragment of 330 bp at the tail end of the DNA insert in the segmental sequencing process was sequenced. At the end of the first sequencing, the newly synthesized DNA strands were blocked by the ddNTP mixture.
   13). After denaturing double-stranded DNA by incubation with 0.5M NaOH for 10 minutes, the newly synthesized strands in the above sequencing step were eluted.
   14). The above steps 6) and 7) were repeated in sequence, and the second round of PW was run for 84 rounds (about 340 bp) of polymerization/cleavage reaction.
   15). The above steps 9)-11) were repeated in sequence, and the second round of sequencing of the fragment 330 bp at the middle of the DNA insert. At the end of this round of sequencing, the newly synthesized DNA strands were blocked by using the ddNTP mixture again.
   16). The newly synthesized strands in the second round of sequencing were eluted after incubation with 0.5M NaOH for 10 minutes to denature the double-stranded DNA.
   17). The above steps 10)-11) were repeated in sequence, and the final round of sequencing of the fragment of 330 bp at the front end of the DNA insert in the segmental sequencing flow was carried out.
   18). The instrument was cleaned according to the instruction manual of the ILLUMINA® gene sequencer.
   19) DNA sequences obtained by the three rounds of sequencing were analyzed and spliced into a complete 1000 bp DNA insert.

3. Experimental Results

Compared with the existing single-ended sequencing technology (i.e., sequencing an insert with a length of 400 bp in *Escherichia coli* by using the ILLUMINA® sequencing platform), the insert with a length of 400 bp corresponds to the first segment of the sequence and part of the middle segment of the sequence of the segmental sequencing of the present disclosure. The comparison results are as follows:

TABLE 2

Sequencing results.

|  | Single-ended sequencing 400bp | First round of sequencing in segmental sequencing (330bp) | Second round of sequencing in segmental sequencing (330bp) | Third round in segmental sequencing (340bp) |
| --- | --- | --- | --- | --- |
| Q30% | 81.12 | 92.6 | 93.0 | 93.7 |
| ESR % | 88.56 | 89.77 | 90.63 | 90.98 |
| Mapping rate % | 89.33 | 95.7 | 96.4 | 96.9 |
| Avg Error rate % | 1.82 | 0.18 | 0.14 | 0.15 |

Figure 9:
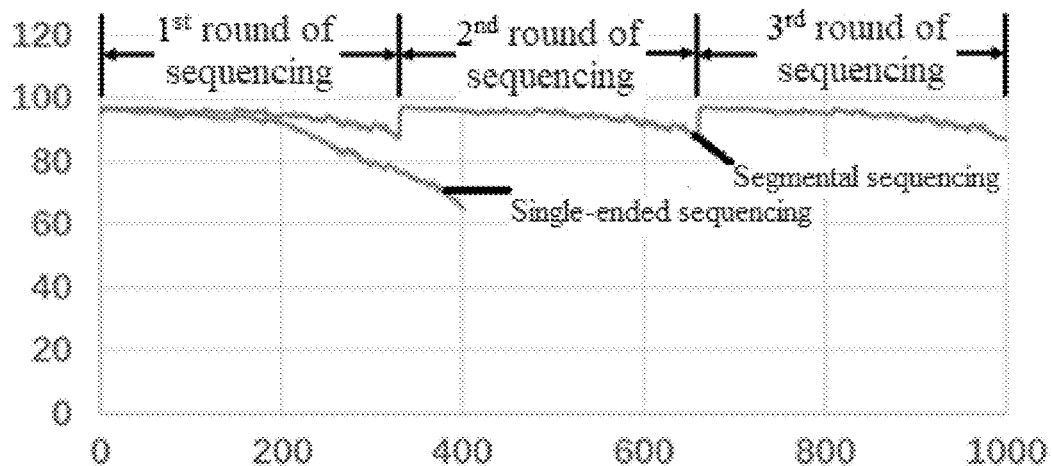
FIG. 9 is a schematic diagram of a sequencing mass ratio (Q30) distribution according to an embodiment of the present disclosure.

The result of Q30 is shown in FIG. 9. The Q30, ESR, mapping rate, and avg. error rate shown in Table 2 have the same meanings as those shown in Table 1. It can be seen from Table 2 and FIG. 9 that the performance of the segmental sequencing technology in various important sequencing quality indicators, including Q30, ESR, mapping rate, and avg. error rate are obviously superior to the former and higher the current requirements for sequencing quality, satisfying the requirements for reading long sequences.

In the description of the present disclosure, the terms "first", "second", etc. are only used for descriptive purposes, and cannot be understood as indicating or implying relative importance or implicitly indicating the number of indicated technical features. Therefore, the features defined with "first" and "second" can include at least one of the features explicitly or implicitly. In the description of the present disclosure, "a plurality of" means at least two, for example, two, three, etc., unless otherwise specifically defined.

In the description of the present disclosure, the terms "one embodiment", "some embodiments", "example", "specific example", or "some examples" mean that specific features, structures, materials or characteristics described in connection with the embodiment or example are included in at least one embodiment or example of the present disclosure. In the specification, the above terms do not necessarily refer to the same embodiments or examples. Furthermore, the specific features, structures, materials or characteristics described may be combined in any one or more embodiments or examples in a suitable manner. In addition, those skilled in the art can combine and assemble different embodiments or examples and features of different embodiments or examples described in this specification without contradicting each other.

Although the embodiments of the present disclosure are illustrated and described above, it can be understood that the above-mentioned embodiments are exemplary and cannot be understood as limitations of the present disclosure. Those skilled in the art can make changes, modifications, substitutions and variations to the above-mentioned embodiments within the scope of the present disclosure.

What is claimed is:

1. A method for determining a nucleic acid sequence of a nucleic acid molecule of a plurality of nucleic acid molecules, wherein an insert of the nucleic acid molecule to be detected is at least 700 bp and is divided into a plurality of predetermined regions, the predetermined region being a first region, a second region, or a third region; the first region, the second region, and the third region are sequentially connected, and sizes of the first region, the second region, and the third region are approximately the same, the method comprising:

step 1' of determining nucleic acid sequences of the first region, the second region, and the third region of the nucleic acid molecule to be detected, respectively; and step 2' of determining the nucleic acid sequence of the nucleic acid molecule based on a result of the step 1';

wherein step 1' further comprises:

step a' of providing two ends of the insert with a first sequencing adapter and a second sequencing adapter, respectively, wherein the first sequencing adapter is connected with one end of the insert and the second sequencing adapter is connected with the other end of the insert;

step b' of hybridizing a plurality of repressor primers with a fraction of the plurality of nucleic acid molecules to be detected, and performing a first extension treatment on the other fraction of the plurality of nucleic acid molecules by using a first dNTP mixture and a sequencing primer, wherein the repressor primers have the same nucleic acid sequence as the sequencing primer, and a 3'-end of each repressor primer comprises a repressor group; the sequencing primer hybridizes to the first sequencing adapter or the second sequencing adapter, and the sequencing primer extends to upstream of the first region;

step c' of performing a second extension treatment on a product of the first extension treatment by using a second dNTP mixture, wherein the nucleic acid sequence of the first region is determined in the second extension treatment, wherein the first dNTP mixture comprises dATP, dTTP, dGTP, and dCTP, at least one of the dATP, dTTP, dGTP, and dCTP carrying a polymerase reaction blocking group; and the second dNTP mixture comprises dATP, dTTP, dGTP, and dCTP, each of the dATP, dTTP, dGTP, and dCTP carrying a polymerase reaction blocking group, and at least one of the dATP, dTTP, dGTP, and dCTP carrying a detectable group;

step d' of cleaving and removing the repressor group of a fraction of the plurality of repressor primers, resulting in a first plurality of unblocked repressor primers, and determining the nucleic acid sequence of the second region of the nucleic acid molecule by performing a third extension treatment and a fourth extension treatment, wherein the first plurality of unblocked repressor primers are extended to upstream of the second region after the first extension treatment; wherein the third extension treatment employs the first dNTP mixture; and the fourth extension treatment employs the second dNTP mixture; and step e' of cleaving and removing the repressor group of the remaining plurality of repressor primers, resulting in a second plurality of unblocked repressor primers and determining the nucleic acid sequence of the third region of the nucleic acid molecule to be detected by performing a fifth extension treatment, wherein the fifth extension treatment employs the second dNTP mixture.

2. The method according to claim 1, wherein the first extension treatment comprises:

step 1 of annealing the nucleic acid molecule to be detected and the sequencing primer to form an initial duplex, the initial duplex consisting of the nucleic acid molecule to be detected and the sequencing primer;

step 2 of incorporating, by using a primer in the initial duplex as a first initial growth nucleic acid strand, at least one dNTP of the first dNTP mixture to a 3'-end of the initial growth nucleic acid strand under catalysis of a polymerase to elongate at least one base at the 3'-end of the initial growth nucleic acid strand, and forming a first product duplex;

step 3 of cleaving the first product duplex to remove, if present, the polymerase reaction blocking group on the first product duplex; and step 4 of repeating the steps 2 to 3 until the sequencing primer extends to a predetermined position upstream of the predetermined region.

3. The method according to claim 1, wherein each of the dATP, dTTP, dGTP, and dCTP in the first dNTP mixture carries the polymerase reaction blocking group; or only one of the dATP, dTTP, dGTP, and dCTP in the first dNTP mixture carries one polymerase reaction blocking group; or at most three of the dATP, dTTP, dGTP, and dCTP in the first dNTP mixture carry the polymerase reaction blocking group, and wherein none of the dATP, dTTP, dGTP, and dCTP in the first dNTP mixture carries the detectable group.

4. The method according to claim 2, wherein in the step 4, the predetermined position is located within 1-100 bp upstream of the predetermined region.

5. The method according to claim 1, wherein the product of the first extension treatment has a length ranging from 200 bp to 600 bp.

6. The method according to claim 2, wherein in the step 4, a distance between the predetermined position and an end downstream of the predetermined region is smaller than or equal to 400 bp.

7. The method according to claim 1, wherein the second extension treatment comprises:

step a of incorporating, by using the product of the first extension treatment as a starting point, one dNTP of the second dNTP mixture to the 3'-end of the product of the first extension treatment under the catalysis of a polymerase to elongate a new base at the 3'-end of the product of the first extension treatment, forming a second product duplex, and determining a type of the new base by detecting the detectable group of the second product duplex;

step b of cleaving the second product duplex to remove the polymerase reaction blocking group and, if present, the detectable group on the second product duplex; and step c of repeating the steps a to b until types of bases of the predetermined region are partially determined.

8. The method according to claim 7, wherein the detectable group is a fluorescent group or a phosphorescent group.

9. The method according to claim 1, wherein the insert of the nucleic acid molecule to be detected is about 1000 bp; a distance between a starting position of the first region and an end upstream of the insert is at least 600 bp, for example 660 bp; a distance between a starting position of the second region and the end upstream of the insert is at least 300 bp, for example 330 bp; and a starting position of the third region is the end upstream of the insert.

10. The method according to claim 9, wherein the repressor groups of the repressor primers are cleaved and removed by an endonuclease.

11. The method according to claim 1, wherein the nucleic acid sequence of the third region of the nucleic acid molecule to be detected is determined without performing the first extension treatment.

12. A method for determining a nucleic acid sequence of a nucleic acid molecule to be detected, wherein an insert of the nucleic acid molecule to be detected is at least 700 bp, the method comprising:
   step A of dividing the insert of the nucleic acid molecule to be detected into a plurality of regions, each of the plurality of regions smaller than or equal to 400 bp, preferably smaller than or equal to 300 bp, and determining, with the method according to claim 1, a nucleic acid sequence of each of the plurality of regions of the nucleic acid molecule to be detected; and
   step B of determining the nucleic acid sequence of the nucleic acid molecule based on a result of the step A.

* * * * *